(12) United States Patent
Sanwal et al.

(10) Patent No.: US 8,916,716 B2
(45) Date of Patent: Dec. 23, 2014

(54) PROCESS FOR THE PREPARATION OF CRYSTALLINE FORM II OF L-MALIC ACID SALT OF SUNITINIB

(75) Inventors: Sudhir Singh Sanwal, Kangra (IN); Saridi Madhava Dileep Kumar, Gurgaon (IN); Swargam Sathyanarayana, Karim Nagar (IN)

(73) Assignee: Ranbaxy Laboratories Limited, New Delhi (IN)

( * ) Notice: Subject to any disclaimer, the term of this patent is extended or adjusted under 35 U.S.C. 154(b) by 205 days.

(21) Appl. No.: 13/510,986

(22) PCT Filed: Nov. 19, 2010

(86) PCT No.: PCT/IB2010/002967
§ 371 (c)(1),
(2), (4) Date: Dec. 5, 2012

(87) PCT Pub. No.: WO2011/061613
PCT Pub. Date: May 26, 2011

(65) Prior Publication Data
US 2013/0197242 A1     Aug. 1, 2013

(30) Foreign Application Priority Data
Nov. 19, 2009   (IN) ............................ 2386/DEL/2009

(51) Int. Cl.
*C07D 403/06*      (2006.01)

(52) U.S. Cl.
CPC .................................... *C07D 403/06* (2013.01)
USPC ......................................................... 548/468

(58) Field of Classification Search
USPC ......................................................... 548/468
See application file for complete search history.

(56) References Cited

U.S. PATENT DOCUMENTS

| | | | |
|---|---|---|---|
| 6,573,293 B2 | 6/2003 | Tang et al. | 514/414 |
| 7,125,905 B2 | 10/2006 | Tang et al. | 514/414 |
| 2003/0069298 A1 | 4/2003 | Hawley et al. | 514/414 |
| 2007/0191458 A1 | 8/2007 | Hawley et al. | 514/414 |
| 2012/0220783 A1* | 8/2012 | Sanwal et al. | 548/468 |
| 2013/0123511 A1* | 5/2013 | Sanwal et al. | 548/468 |
| 2013/0210885 A1* | 8/2013 | Sanwal et al. | 514/414 |

FOREIGN PATENT DOCUMENTS

| | | | | |
|---|---|---|---|---|
| EP | 2 186 809 | 5/2010 | ........... | C07D 403/06 |
| WO | WO 2004/012776 | 2/2004 | ........... | A61K 51/04 |
| WO | WO 2009/067686 | 5/2009 | ........... | C07D 403/06 |
| WO | WO 2009/104021 | 8/2009 | ........... | C07D 403/06 |
| WO | WO 2010/076805 | 7/2010 | ........... | C07D 403/06 |

\* cited by examiner

*Primary Examiner* — Nyeemah A Grazier

(57) ABSTRACT

The present invention relates to stable crystalline Form II of L-malic acid salt of sunitinib and its preparation.

11 Claims, 4 Drawing Sheets

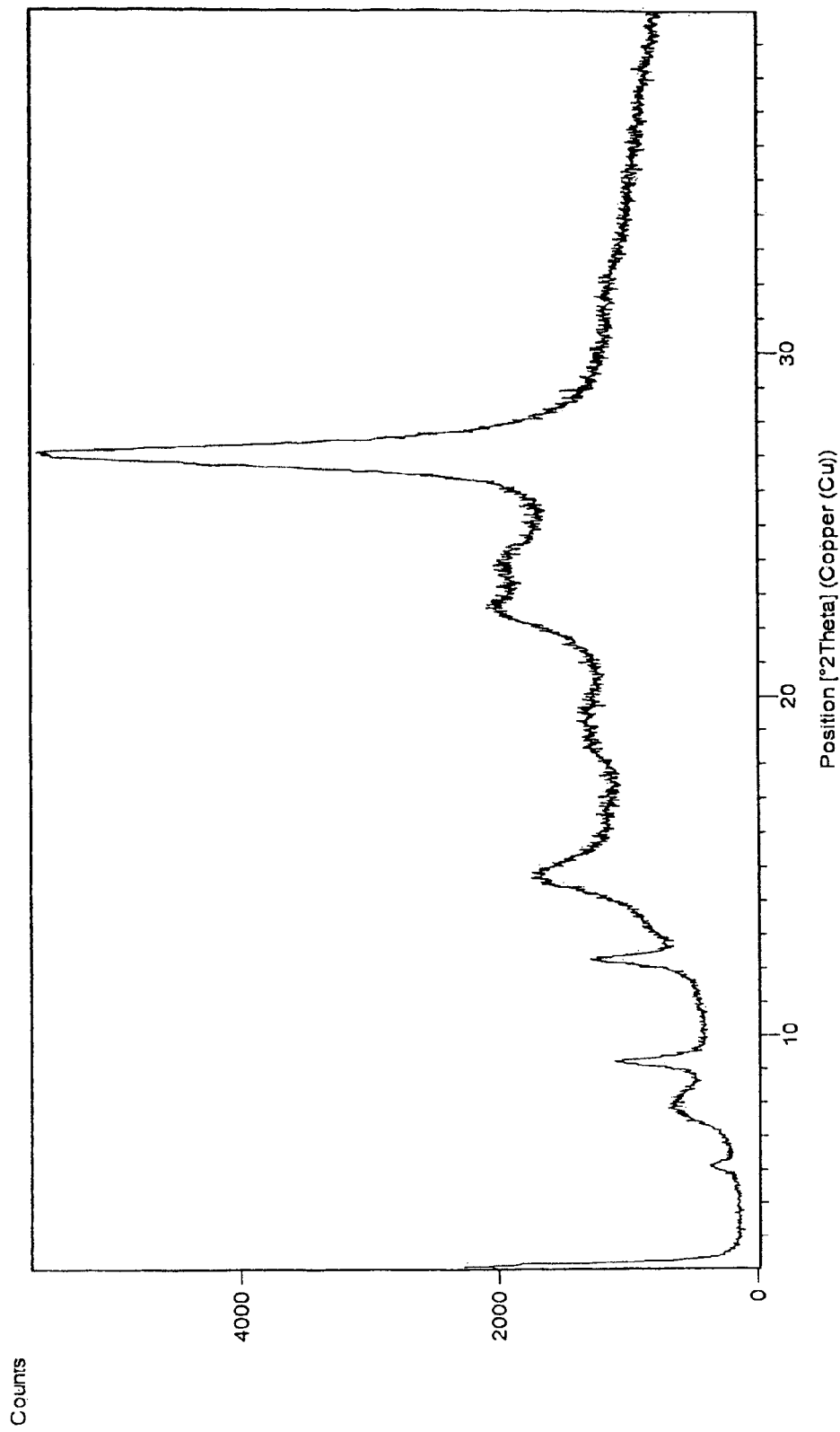
FIGURE 1: XRPD OF CRYSTALLINE FORM II OF L-MALIC ACID SALT OF SUNITINIB

FIGURE 1A: TABLE OF VALUES FOR THE XRPD PATTERN DEPICTED IN FIGURE 1

| Pos [° 2Th] | d-spacing [Å] | Rel. Int [%] |
|---|---|---|
| 3.08 | 28.65 | 51.05 |
| 6.14 | 14.40 | 3.71 |
| 7.77 | 11.37 | 8.71 |
| 9.23 | 9.59 | 16.84 |
| 12.24 | 7.23 | 15.66 |
| 14.55 | 6.09 | 14.96 |
| 22.58 | 3.94 | 16.37 |
| 24.08 | 3.70 | 13.45 |
| 27.03 | 3.30 | 100.00 |

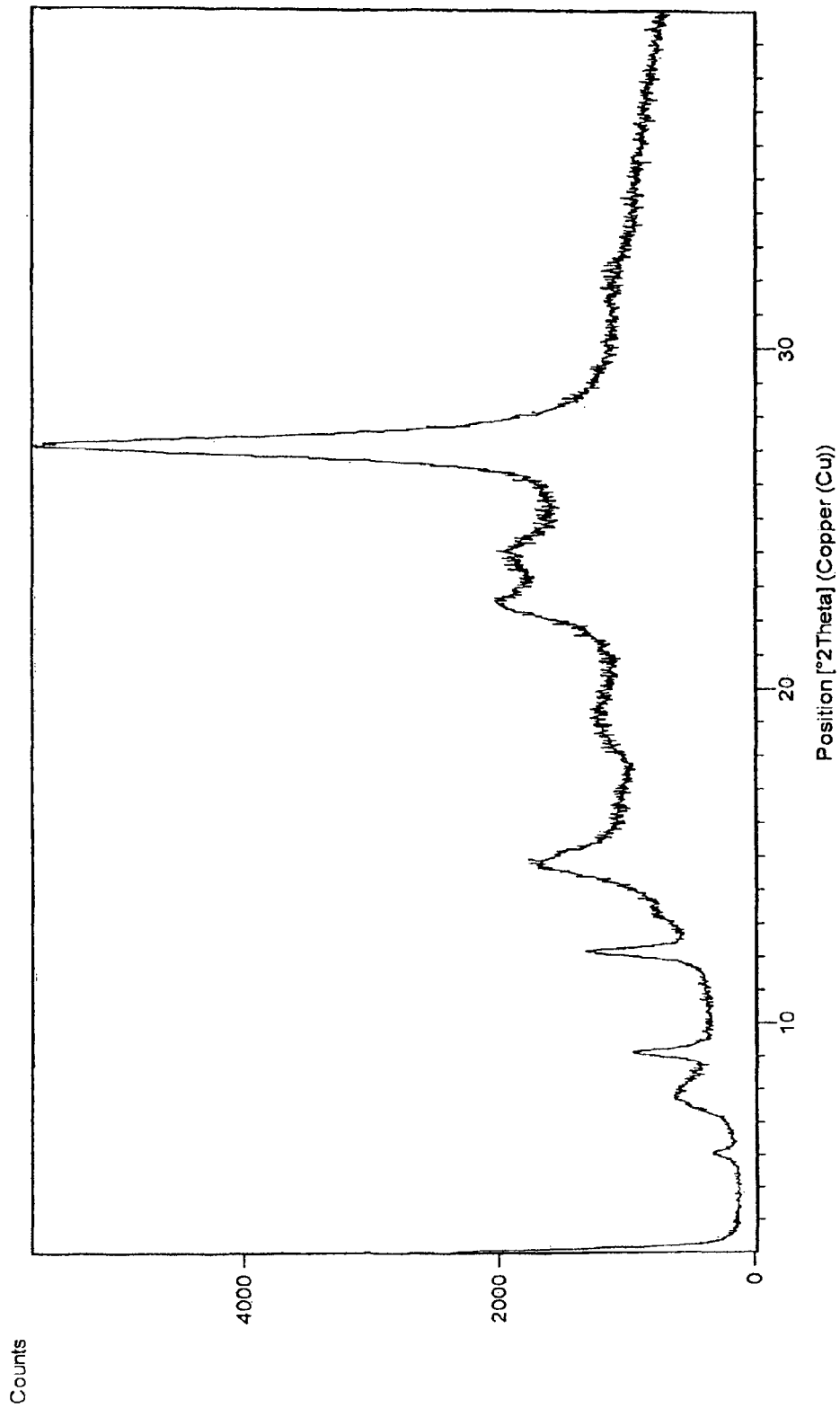

FIGURE 2A: TABLE OF VALUES FOR THE XRPD PATTERN DEPICTED IN FIGURE 2

| Pos [° 2Th] | d-spacing [Å] | Rel. Int [%] |
| --- | --- | --- |
| 3.05 | 28.94 | 49.05 |
| 6.06 | 14.57 | 3.55 |
| 7.75 | 11.41 | 8.96 |
| 9.13 | 9.69 | 14.70 |
| 12.14 | 7.29 | 18.20 |
| 14.85 | 5.96 | 19.68 |
| 22.41 | 3.97 | 19.03 |
| 24.06 | 3.70 | 16.09 |
| 27.01 | 3.30 | 100.00 |

PROCESS FOR THE PREPARATION OF CRYSTALLINE FORM II OF L-MALIC ACID SALT OF SUNITINIB

FIELD OF THE INVENTION

The present invention relates to stable crystalline Form II of a L-malic acid salt of sunitinib and a process for the preparation thereof.

BACKGROUND OF THE INVENTION

Sunitinib is chemically described as N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide as represented by Formula I.

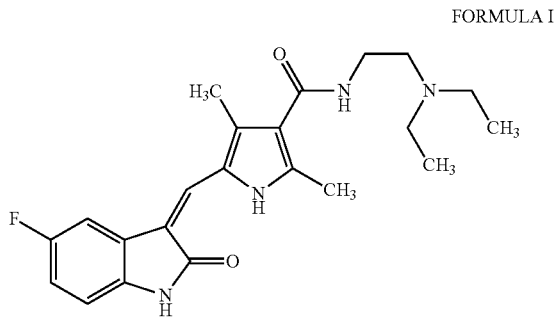 [SMILES: CCN(CC)CCNC(=O)c1c(C)[nH]c(/C=C2\C(=O)Nc3ccc(F)cc32)c1C]

FORMULA I

Sunitinib is an oral multi-kinase inhibitor and useful for the treatment of gastrointestinal stromal tumor and advanced renal cell carcinoma. Sunitinib is commercially available as the L-malate salt, which is described chemically as butanedioic acid, hydroxy-, (2S)—, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1).

U.S. Patent Application Nos. 2003/0069298 and 2007/0191458 describe the preparation of crystalline Forms I and II of L-malic acid salt of sunitinib. According to these applications, crystalline Form I of L-malic acid salt of sunitinib is prepared by slurrying a poorly crystalline or crystalline Form II of L-malic acid salt of sunitinib in acetonitrile. Crystalline Form II of the L-malic acid salt of sunitinib is prepared by dissolving crystal Form I of L-malic acid salt of sunitinib in tetrahydrofuran and water and allowing the solvent to evaporate overnight.

WO 2009/067686 describes processes for preparing crystalline Forms of racemic sunitinib malate, sunitinib hemi-L-malate and compositions containing sunitinib base and L- or racemic malic acid.

WO 2009/104021 describes processes for preparing crystalline Forms III and IV of sunitinib L-malate.

WO 2009/104021 describes that Form II of sunitinib L-malate is hygroscopic, thermodynamically unstable and appears to readily convert to Form I.

SUMMARY OF THE INVENTION

In one general aspect, the present invention provides for a stable crystalline Form II of L-malic acid salt of sunitinib.

Embodiments of this aspect may include one or more of the following aspects. For example, the stable crystalline Form II of L-malic acid salt does not convert into any other solid form on storage of about 20 days or more. The stable crystalline Form II of L-malic acid salt absorbs moisture to a level of not more than about 2%.

In another general aspect, the present invention provides for a process for the preparation of crystalline Form II of L-malic acid salt of sunitinib. The process includes:
a) charging a solution of L-malic acid salt of sunitinib in a solvent to a spray dryer;
b) removing the solvent from the solution obtained in step a) by spray drying; and
c) collecting crystalline Form II of L-malic acid salt of sunitinib from the spray dryer.

Embodiments of this aspect may include one or more of the following features. For example, the solvent may be water, an alkanol, such as methanol, or a mixture thereof.

BRIEF DESCRIPTION OF THE DRAWINGS

FIG. 1 depicts the X-ray powder diffraction pattern (XRPD) of the stable crystalline Form II of L-malic acid salt of sunitinib.

FIG. 1A provides table of values for the XRPD pattern depicted in FIG. 1.

FIG. 2 depicts the X-ray powder diffraction pattern (XRPD) of the stable crystalline Form II of L-malic acid salt of sunitinib after the storage of 24 days.

FIG. 2A provides table of values for the XRPD pattern depicted in FIG. 2.

DETAILED DESCRIPTION OF THE INVENTION

The term "L-malic acid salt of sunitinib" includes a combination of sunitinib and L-malic acid in any molar ratio between about 1:0.75 and about 1:1.5.

The term "charging", according to the present invention, includes loading, filling, introducing, pouring, infusing and/or adding.

The term "collecting", according to the present invention, includes unloading, gathering and/or scaling.

The present invention provides a stable crystalline Form II of L-malic acid salt of sunitinib. The stable crystalline Form II of L-malic acid salt of sunitinib has an XRPD pattern wherein the characteristic 2θ values are obtained substantially at 3.08±0.2, 6.14±0.2, 7.77±0.2, 9.23±0.2, 12.24±0.2, 14.55±0.2, 22.58±0.2, 24.08±0.2 and 27.03±0.2 degree 2θ. The stable crystalline Form II of L-malic acid salt does not convert into any other solid form upon storage for about 20 days or more. The stable crystalline Form II of L-malic acid salt absorbs moisture to a level of not more than about 2%, for example, not more than between about 1% to about 1.5%.

The present invention also provides for a process for the preparation of crystalline Form II of L-malic acid salt of sunitinib. The process includes:
a) charging a solution of L-malic acid salt of sunitinib in a solvent to a spray dryer;
b) removing the solvent from the solution obtained in step a) by spray drying; and
c) collecting crystalline Form II of L-malic acid salt of sunitinib from the spray dryer.

L-Malic acid salt of sunitinib existing in any solid form prepared by any method known in literature, for example, U.S. Pat. Nos. 6,573,293 and 7,125,905; and WO 2004/012776 may be used for preparing the solution of L-malic acid salt of sunitinib in a solvent.

The solution of L-malic acid salt of sunitinib in a solvent may also be prepared by dissolving sunitinib base and L-malic acid in a solvent. The solvent may be water or an alkanol, for example, methanol, or a mixture thereof. The solution may optionally be filtered prior to charging to the spray dryer. The inlet and outlet temperatures, feed rate, and atomizer type may be adjusted to optimize output and particle size. The air inlet temperature may be controlled from about 60° C. to about 150° C., for example, about 100° C. to about 140° C. The outlet temperature may be controlled from about 30° C. to about 80° C., for example, about 50° C. to about 70° C. An inert gas, for example, nitrogen gas can be used as a carrier gas. After spray drying, the crystalline Form II of L-malic acid salt of sunitinib is collected from the spray dryer and optionally further dried under vacuum to remove the residual solvents. The crystalline Form II of L-malic acid salt of sunitinib so obtained is stable and has substantially the same XRPD pattern as depicted in FIG. 1.

The XRPD of the samples were determined by using Panalytical X'Pert Pro X-Ray Powder Diffractometer in the range 3-40 degree 2 theta and under tube voltage and current of 45 Kv and 40 mA respectively. Copper radiation of wavelength 1.54 angstrom and Xceletor detector was used.

While the present invention has been described in terms of its specific embodiments, certain modifications and equivalents will be apparent to those skilled in the art and are intended to be included within the scope of the present invention.

EXAMPLE

Example 1

Preparation of Stable Crystalline Form Ii of L-Malic Acid Salt of Sunitinib L-Malic acid salt of sunitinib (3 g) was dissolved in water (300 ml) at 40° C. The solution was filtered, cooled to 20° to 25° C., and charged to a spray dryer (BUCHI mini spray dryer B-290) at feed pump RPM of 7. The following parameters were controlled in the spray drying process:

Nozzle Diameter: 0.7 mm
Carrier gas: Nitrogen at 2.0 to 2.5 kg/cm$^2$
Air inlet temperature: 130° C.
Outlet temperature: 60° C.
Aspiration: 70%
Type of atomizer: Co current flow (also known as to fluid pressure nozzle)

The solvent was evaporated at a temperature of about 60° C. to about 65° C. through spray drying. The solid so obtained was collected from the spray dryer to obtain the title compound having an XRPD pattern as depicted in FIG. 1 initially and an XRPD pattern as depicted in FIG. 2 after storage at 20° C. to 25° C. for 24 days.

Yield: 1.5 g
Moisture content by KF: 4.48% (initial)
Moisture content by KF: 5.52% (after storage at 20° C. to 25° C. for 60 days)

We claim:

1. A stable crystalline Form II of L-malic acid salt of sunitinib having an XRPD pattern wherein the characteristic d-spacing values are obtained substantially at 28.65, 14.40, 11.37, 9.59, 7.23, 6.09, 3.94, 3.70, and 3.30±0.3 degree 2θ.

2. The stable crystalline Form II of L-malic acid salt of sunitinib according to claim 1, wherein the stable crystalline Form II of L-malic acid salt does not convert into any other solid form on storage of about 20 days or more.

3. The stable crystalline Form II of L-malic acid salt of sunitinib according to claim 1, wherein the stable crystalline Form II of L-malic acid salt absorbs moisture to a level of not more than about 2%.

4. A process for the preparation of stable crystalline Form II of L-malic acid salt of sunitinib having an XRPD pattern wherein the characteristic d-spacing values are obtained substantially at 28.65, 14.40, 11.37, 9.59, 7.23, 6.09, 3.94, 3.70, and 3.30±0.3 degree 2θ, wherein the process comprises:
   a) charging a solution of L-malic acid salt of sunitinib in a solvent to a spray dryer;
   b) removing the solvent from the solution obtained in step a) by spray drying; and
   c) collecting stable crystalline Form II of L-malic acid salt of sunitinib from the spray dryer.

5. The process according to claim 4, wherein the solvent is water, an alkanol, or a mixture thereof.

6. The process according to claim 5, wherein the alkanol is methanol.

7. The stable crystalline Form II of L-malic acid salt of sunitinib of claim 3, wherein the crystalline form is produced by spray drying.

8. The stable crystalline Form II of L-malic acid salt of sunitinib of claim 7, wherein the spray drying comprises spray drying a solution of L-malic acid salt of sunitinib in a solvent.

9. The stable crystalline Form II of L-malic acid salt of sunitinib of claim 8, wherein the solvent comprises water, an alkanol, or a mixture thereof.

10. The stable crystalline Form II of L-malic acid salt of sunitinib of claim 9, wherein the alkanol comprises methanol.

11. A spray dried stable crystalline Form II of L-malic acid salt of sunitinib according to claim 3.

* * * * *

UNITED STATES PATENT AND TRADEMARK OFFICE
CERTIFICATE OF CORRECTION

PATENT NO. : 8,916,716 B2
APPLICATION NO. : 13/510986
DATED : December 23, 2014
INVENTOR(S) : Sudhir Singh Sanwal et al.

It is certified that error appears in the above-identified patent and that said Letters Patent is hereby corrected as shown below:

In the specification

COLUMN 3, LINE 32:

"Preparation of Stable Crystalline Form Ii of L-Malic"

should read

-- Preparation of Stable Crystalline Form II of L-Malic --

Signed and Sealed this
Thirteenth Day of October, 2015

Michelle K. Lee
*Director of the United States Patent and Trademark Office*